United States Patent [19]

Khazaka et al.

[11] Patent Number: 5,684,573
[45] Date of Patent: Nov. 4, 1997

[54] DEVICE AND METHOD FOR MEASURING A THREE-DIMENSIONAL SURFACE STRUCTURE

[75] Inventors: Gabriel Khazaka; Wilfried Courage, both of Cologne, Germany

[73] Assignee: Courage & Khazaka Electronic GmbH, Cologne, Germany

[21] Appl. No.: 513,955

[22] PCT Filed: Mar. 2, 1994

[86] PCT No.: PCT/EP94/00612

§ 371 Date: Sep. 1, 1995

§ 102(e) Date: Sep. 1, 1995

[87] PCT Pub. No.: WO94/20019

PCT Pub. Date: Sep. 15, 1994

[30] Foreign Application Priority Data

Mar. 3, 1993 [DE] Germany ............................ 9303102 U

[51] Int. Cl.⁶ .................................................. B29C 33/40
[52] U.S. Cl. ........................... 356/36; 356/371; 264/40.1
[58] Field of Search ........................ 356/36, 244, 371, 356/71

[56] References Cited

U.S. PATENT DOCUMENTS 4,279,482 7/1981 Tyson ............................... 356/71
4,569,358 2/1986 Gormley ........................... 356/376
5,211,894 5/1993 Groh et al. ...................... 264/40.1

FOREIGN PATENT DOCUMENTS 2658713  2/1990  France.
2719341  4/1977  Germany.
59043358 9/1982  Japan.

Primary Examiner—Richard A. Rosenberger
Attorney, Agent, or Firm—Diller, Ramik & Wight

[57] ABSTRACT

In a device for measuring a three-dimensional surface structure, in particular skin folds of a human skin surface (9), comprising a transparent support plate (2) for receiving initially liquid silicone material (3) for a silicone impression of the measurement surface and comprising an analyzing unit for analyzing the surface structure of the impression, it is provided, according to the invention, that the support plate (2) comprises a measurement zone (4) which is held at a given distance from the measurement surface (9), that the silicone material (3) to be introduced into the measurement zone (4) is uniformly colored, and that the support plate (2) comprises at least one drainage channel (10) for excess silicone material (3) leading away from the measurement zone (4). The analysis of the silicone impression is effected via a light intensity measurement of the light absorption of the silicone impression.

25 Claims, 3 Drawing Sheets

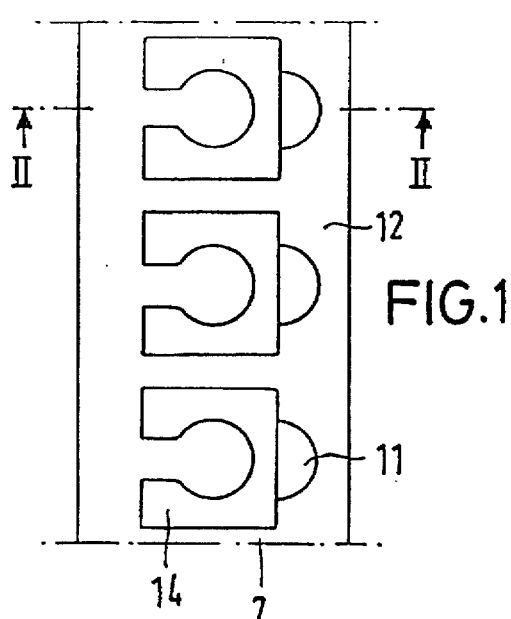
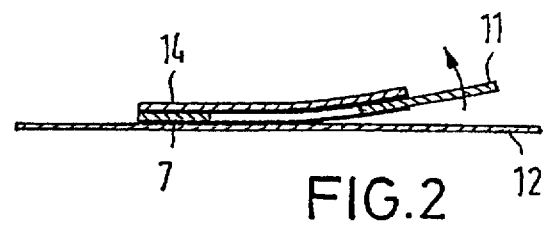
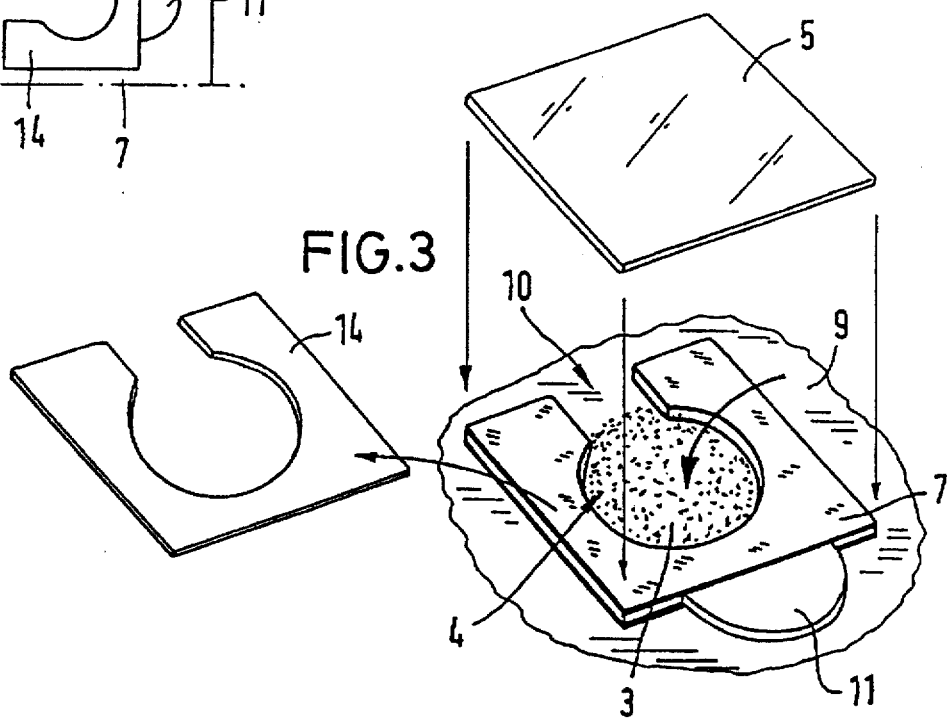
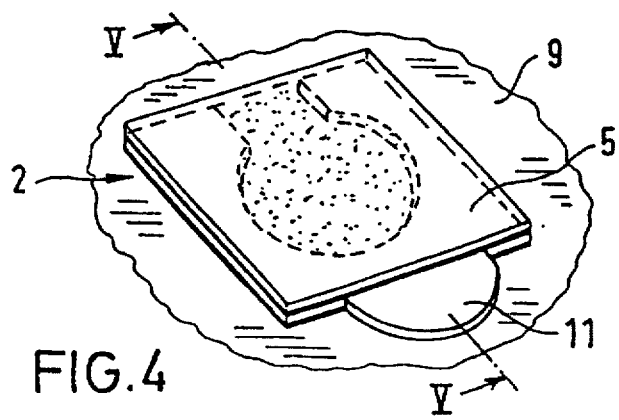
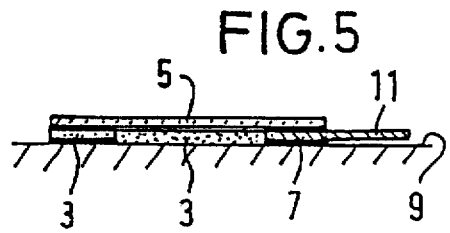

DEVICE AND METHOD FOR MEASURING A THREE-DIMENSIONAL SURFACE STRUCTURE

BACKGROUND OF THE INVENTION

The invention relates to a device for measuring a three-dimensional surface structure.

One application area of such measuring devices is the examination of the skin surface for the skin cosmetic. In this area, it is desired to three-dimensionally map the skin structure as exactly as possible, a very high resolution of the measured values being essential for the purpose of proving the effect of skin treatment preparation in order to be able to detect changes in skin structure at intervals of time.

Other application examples from technics relate to wood surfaces or metal surfaces.

It is already known to make silicone impressions of the skin surface and to subsequently obliquely illuminate the impression to get information on the three-dimensional structure corresponding to the casting of the shadow. Such a measurement has the disadvantage to be dependent on distance and light incidence angle of the light source, the analysis being very time-consuming in addition.

It is also possible to scan the silicone impression by laser, which, however, is expensive.

A further possibility is to scan the impression with a diamond point to generate a three-dimensional image of the skin surface, the accuracy of the three-dimensional image being dependent on the raster resolution of the scanning. Such a measurement is also very time-consuming and not sufficiently accurate due to the dependence on the raster of the scanning. Such a method, for example, is known from DE 27 19 341 C.

In summary, the disadvantage of the known measuring device consists in that the measurements can only be performed by approximation, that the reproducibility of the measured values is low, and that too much time is needed.

SUMMARY OF THE INVENTION

It is the object of the invention to provide a device for measuring a three-dimensional surface structure, which provides measured values which are three-dimensionally analyzable and adapted to be reproduced and calibrated to a great extent, with little time consumption.

The invention advantageously provides that the support plate comprises a measurement zone held at a given distance from the measurement surface. The silicone material to be introduced into the measurement zone is uniformly colored, the support plate comprising at least one drainage channel for excess silicone material leading away from the measurement zone. Thus, it is ensured that the measurement surface is not deformed while making the silicone impression, which would result in measuring faults. It is rather guaranteed by the drainage channel leading away from the measurement surface that the silicone impression can be made pressure-free to the greatest possible extent. The measurement zone is held at a given distance from the measurement surface. Thereby, the layer size of the silicone impression is set to a thickness allowing to detect the entire depth of the three-dimensional surface structure and simultaneously guaranteeing that the layer size does not become too thick, which would make the analysis on the basis of a measurement of light intensity and light absorption, respectively, more difficult. Since the silicone material is uniformly colored, the light absorption of the silicone mass is a direct measure of the layer size of the silicone impression. By means of a suitable optical analyzer, it is possible with such a silicone impression to obtain three-dimensional measured values which are quickly analyzable and adapted to be reproduced and calibrated to a great extent.

In one embodiment, it is provided that the support plate consists of a thin transparent pane and a double-sided adhesive sheet which serves as spacer and in which at least one drainage channel is punched out. Such a support plate assembled from two parts can easily be applied onto skin surfaces and is better adaptable to skin surfaces. Particularly, such a support plate can be manufactured in relatively small dimensions, whereby the support plate's influence on the measurement surface is reduced.

In a second embodiment, it is provided that a step-shaped calibrating means having at least two defined step distances and being directed to the measurement surface is provided within the measurement zone. The steppings of the calibrating means starting from the surface of the measurement zone advantageously permit to exactly allocate certain brightness values of the silicone material to corresponding depth values, so that a calibration of the measured data is advantageously possible and three-dimensional depth values are measurable with high accuracy and reproducibility.

The calibration advantageously allows for the compensation of a possible non-linearity of the measured signals. The silicone impression on the support plate is preferably illuminated with parallel light, the uniformly colored silicone material generating, depending on the layer size, a different brightness value for a detector, e.g., an optical system with CCD means.

Preferably, it is provided that the silicone material is colored with such a uniform intensity that a brightness difference measurable with high resolution is generated for each amount of step of the calibrating means. The absorption density of the silicone material is adapted to a maximum layer size of about 1 mm.

In this manner, 256 brightness values can be distinguished with respect to a layer size of about 1 mm by means of detectors, so that the depth estimation can be effected with extreme high accuracy and reproducibility.

Preferably, the support plate is arranged in a mounting insertable in diascopes. The use of a support plate in a slide frame format permits the quick analysis of the impressions by means of video analyzers.

Next to the measurement zone of the support plate, drainage channels may be led through to the back side of the support plate from all around the measurement zone. The drainage channels permit the transport of excess silicone material and thereby prevent a pressure build-up in the region of the measurement surface. Furthermore, the silicone impression is advantageously anchored on the support plate.

BRIEF DESCRIPTION OF THE DRAWINGS

Hereinafter, an embodiment of the invention is explained in detail with respect to the drawings, in which:

FIG. 1 shows sheets for a support plate of a first embodiment,

FIG. 2 shows a section along the line II—II in FIG. 1,

FIG. 3 shows the application of the first embodiment on the measurement surface, FIG. 4 shows the production of the impression on the measurement surface, FIG. 5 shows a section along the line along the line V—V in FIG. 4.

DESCRIPTION OF THE PREFERRED EMBODIMENTS

Figure 6:
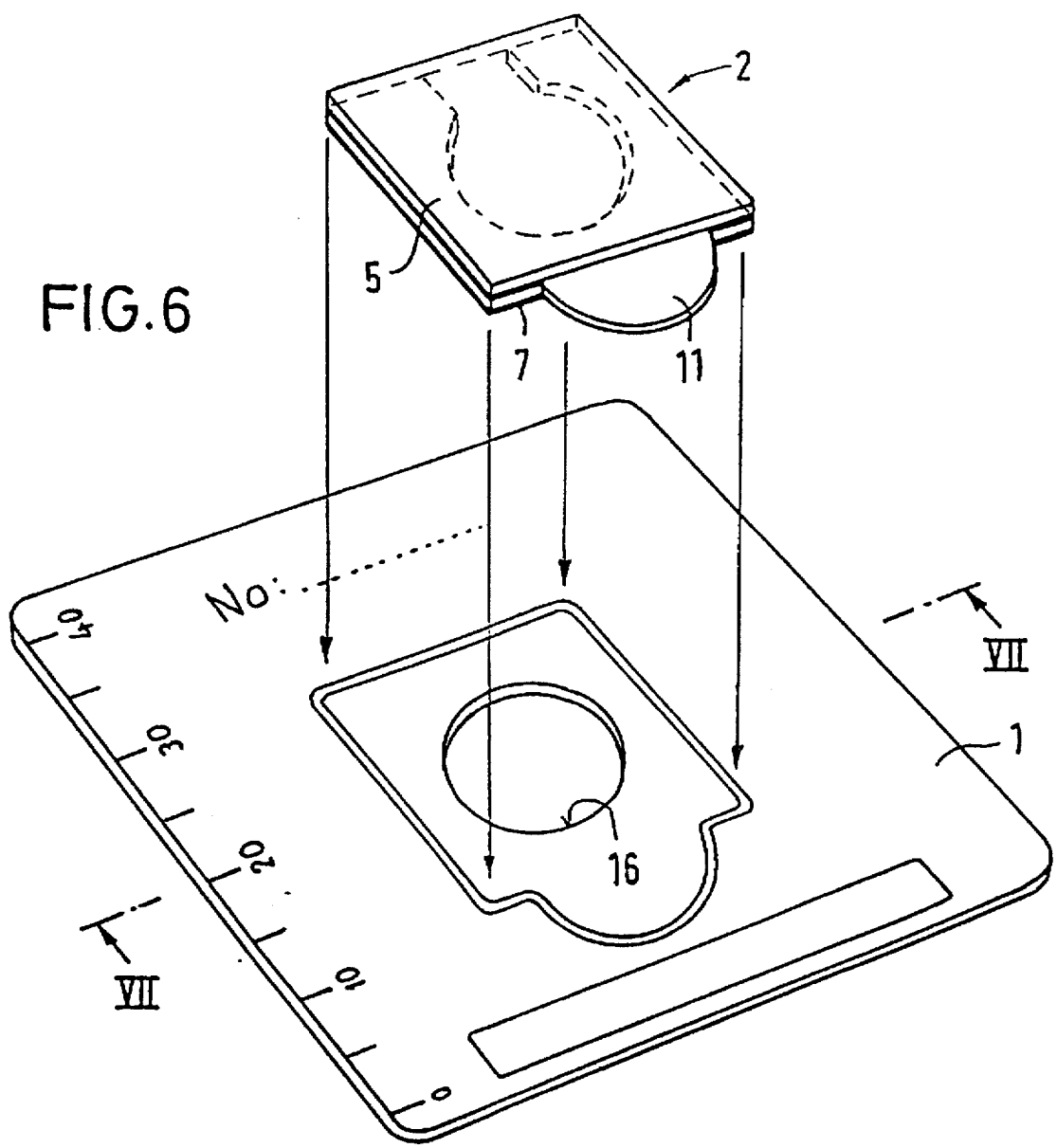
FIG. 6 shows the application of the support plate of the first embodiment onto a frame.
Figure 7:
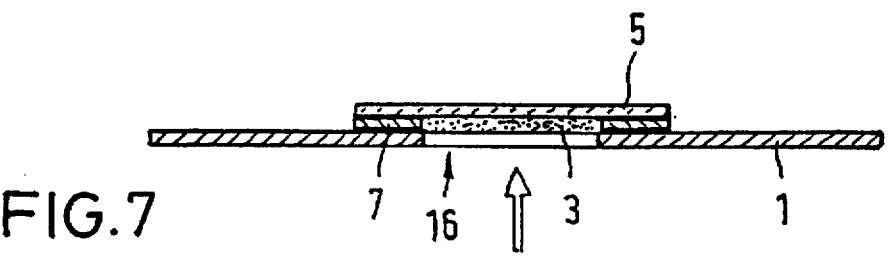
FIG. 7 shows a section along the line VII—VII in FIG. 6.

FIG. 3 shows the application of a first embodiment onto a measurement surface, e.g., a skin surface 9. For that purpose, as can be seen best in FIG. 1, double-sided adhesive sheets 7 located on a sheet support 12 are first removed from the sheet support 12 with the aid of a tag 11 and stuck onto the skin surface 9 at the desired measurement spot.

The sheet 7 consists of a transparent flexible plastic sheet having a thickness of about 0.4 to 0.7 mm, preferably about 0.5 mm, which has in its center a substantially circular punch-out limiting a substantially circular measurement zone 4. A further punch-out produces a drainage channel 10 from the measurement zone 4 to the outside.

The sheets 7 arranged on the sheet support 12 comprise a covering paper 14 which can be removed after the sheet 7 has been applied onto the measurement surface, as shown in FIG. 3.

After the covering paper 14 has been removed, several drops of liquid silicone material 3 are applied onto to the skin surface 9 onto the measurement zone 4 limited by the sheet 7. Subsequently, a transparent pane 5 forming the support plate 2 of the first embodiment together with the sheet 7 is set onto the sheet 7 and firmly sticks thereto on account of the adhesive layer on the sheet 7.

The pane 5 may consist of a thin, preferably coated, glass. When setting on the pane 5, excess silicone material is led to the outside via the drainage channel 10, whereby a pressure-free and hence genuine silicone impression of the measurement surface can be produced. With a pane 5 of glass, the own weight of the pane is sufficient to squeeze out the excess silicone material via the drainage channel 10. After the silicone material 3 has hardened, the support plate 2, i.e. the sheet 7, can be removed from the skin surface 9 together with the pane 5 and the silicone impression by means of the tag 11 and put into an optical analyzer.

The adhesive face of the support plate 2 facing the skin surface can be used to stick the support plate 2 onto a frame 1 which can be inserted in diascopes or video analyzers and is adapted to be suitably labeled. For this purpose, as can be seen in FIG. 6, the frame comprises a central circular opening 16 matching the measurement zone 4 and permitting transillumination of the support plate 2 with the silicone impression.

Figure 9:
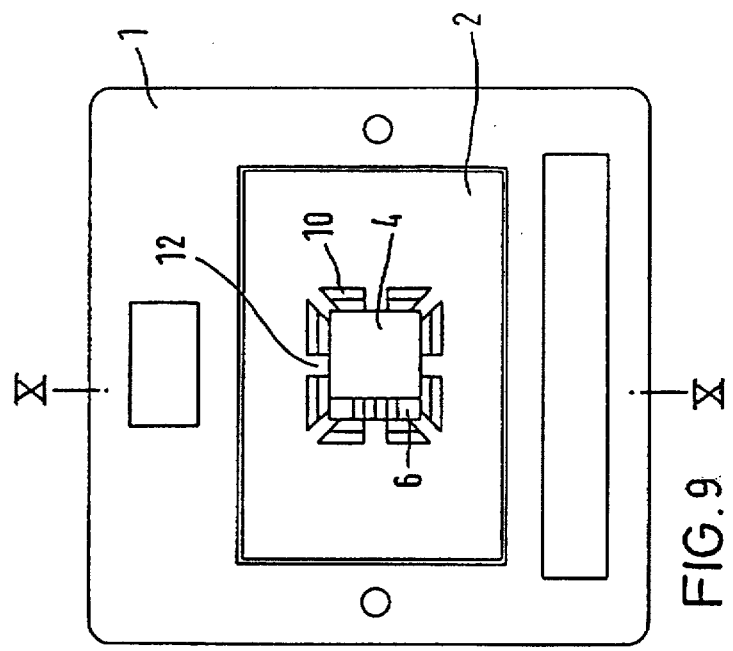
FIG. 9 shows the side of the embodiment according to FIG. 8 which faces the measurement surface.
Figure 8:
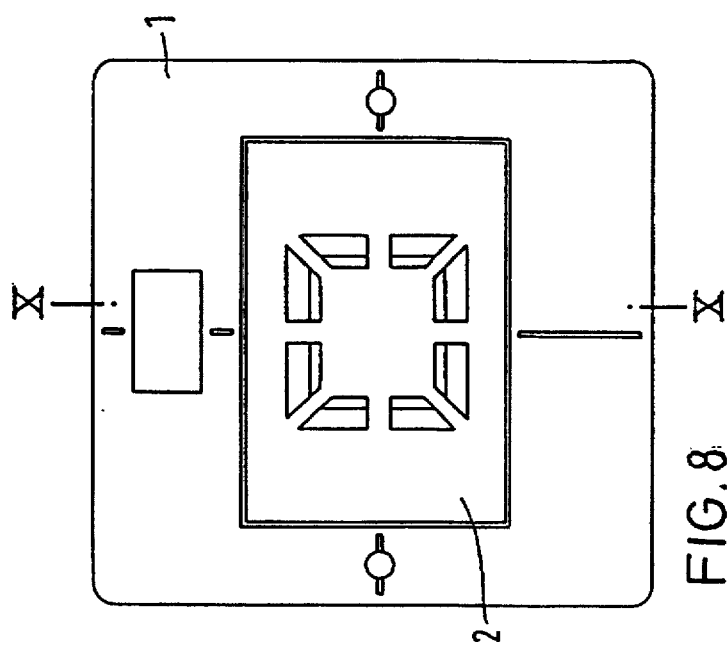
FIG. 8 shows a plan view onto that side of a second embodiment of a support plate set in a frame which faces away from the measurement surface.
Figure 10:
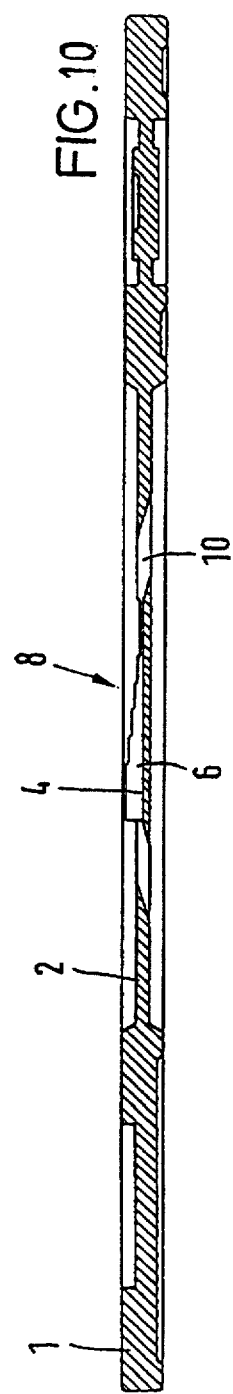
FIG. 10 shows a section along the line X—X in FIGS. 8 and 9.

FIGS. 8, 9 and 10 show a support plate 2 of a second embodiment having an integrated calibrating means and being set in a frame 1. The initially still liquid silicone layer permits to produce a silicone impression of a three-dimensional surface structure, in particular skin folds of a human skin surface.

As to its dimensions, the frame 1 exactly corresponds to commercially available miniature slide holders so that the silicone impression on the support plate 2 can be analyzed by means of diascopes and video analyzers.

The support plate 2 centrally comprises, on the side facing the measurement surface, the measurement zone 4 from one side of which a calibrating means 6 projects towards the measurement surface.

The calibrating means comprises several steppings 8 having exactly defined step distances, so that the uniformly colored silicone material is present in step-like manner in different layer size in the region of the calibrating means 6. Upon transilluminating the silicone impression, certain brightness values of the impression can be allocated to exact measured depth values by means of the steppings. By means of the calibrating means 6, the brightness differences, which are preferably digitally analyzed in the measurement zone, can be exactly calibrated, so that a depth determination of the surface structure, which is highly reproducible and accurate, is possible.

For the first embodiment according to FIGS. 1 to 7, it is also possible to use a separate calibrating means 6, since it is not required to produce another calibrating scale for each impression. It is sufficient, for example, to produce one calibrating impression for each colored silicone charge.

By means of a CCD detector means, it is possible to distinguish 256 brightness values, the depth values of the surface structure normally comprising a structure difference of about 0.5 mm at maximum.

The uniform coloring of the silicone material is adapted to the maximum layer depth of the silicone layer of about 1 mm, so that the resolution of the brightness values is optimized for the measurement depths of interest.

Preferably, the side of the support plate 2 facing away from the measurement surface is coated at least in the region of the measurement zone 4. The support plate 2 is uncolored and consists of glass or plastic. It may be coated.

According to the second embodiment, drainage channels 10 extending radially outward extend obliquely from the outer edge of the measurement zone 4 through the support plate 2. The slit-shaped drainage channels 10 widen radially outward. The drainage channels 10 permit the drainage of excess silicone material during the production of the impression and prevent the build-up of a pressure in the region of the measurement zone which might change the measurement surface. Simultaneously, the silicone material is led away from the back side of the measurement zone 4, so that no silicone material can reach the back side of the measurement zone 4.

Additionally, the drainage channels 10 serve for anchoring the silicone impression on the support plate 2, since the silicone impression is analyzed remaining on the support plate 2.

We claim:

1. A device for measuring a three-dimensional surface structure comprising a transparent support plate (2) for receiving an initially liquid silicone material (3) for a silicone impression of a three-dimensional surface structure (9), and an analyzing unit for analyzing the surface structure of the impression, characterized in that the support plate (2) comprises a measurement zone (4) located at a given distance from the surface structure (9), silicone material (3) adapted to be introduced into the measurement zone (4) is uniformly colored, and the support plate (2) includes at least one drainage channel (10) for excess silicone material (3) leading away from the measurement zone (4).

2. The device according to claim 1, characterized in that the support plate (2) includes a thin transparent pane (5) and a double-sided adhesive sheet (7) which serves as a spacer, and the measurement zone (4) and at least one drainage channel (10) are punched out.

3. The device according to claim 2, characterized in that a step-shaped calibrating means (6) is directed toward the surface structure (9) and includes at least two defined step distances (8) within the measurement zone (4).

4. The device according to claim 2, characterized in that the absorption density of the silicone material (3) is adapted to a maximum layer size of about 1 mm.

5. The device according to claim 2, characterized in that the support plate (2) is arranged in a frame (1) which can be inserted in diascopes and video analyzers.

6. The device according to claim 2, characterized in that the silicone impression remains on the support plate (2) for analysis.

7. The device according to claim 2, characterized in that drainage channels (10) are led through the support plate (2) from the edge of the measurement zone (4).

8. The device according to claim 1 characterized in that a step-shaped calibrating means (6) is directed toward the surface structure (9) and includes at least two defined step distances (8) within the measurement zone (4).

9. The device according to claim 8, characterized in that the silicone material (3) is colored with such a uniform intensity that a brightness difference measurable with high resolution arises for each amount of a step distances (8) of the calibrating means (6).

10. The device according to claim 9, characterized in that the silicone impression remains on the support plate (2) for analysis.

11. The device according to claim 9, characterized in that drainage channels (10) are led through the support plate (2) from the edge of the measurement zone (4).

12. The device according to claim 8, characterized in that the support plate (2) is arranged in a frame (1) which can be inserted in a diascopes and video analyzers.

13. The device according to claim 8, characterized in that the silicone impression remains on the support plate (2) for analysis.

14. The device according to claim 8, characterized in that drainage channels (10) are led through the support plate (2) from the edge of the measurement zone (4).

15. The device according to claim 1, characterized in that the absorption density of the silicone material (3) is adapted to a maximum layer size of about 1 mm.

16. The device according to claim 15, characterized in that the silicone impression remains on the support plate (2) for analysis.

17. The device according to claim 15, characterized in that drainage channels (10) are led through the support plate (2) from the edge of the measurement zone (4).

18. The device according to claim 1, characterized in that the support plate (2) is arranged in a frame (1) which can be inserted in diascopes and video analyzers.

19. The device according to claim 18, characterized in that the silicone impression remains on the support plate (2) for analysis.

20. The device according to claim 18, characterized in that drainage channels (10) are led through the support plate (2) from the edge of the measurement zone (4).

21. The device according to claim 1, characterized in that the silicone impression remains on the support plate (2) for analysis.

22. The device according to claim 21, characterized in that drainage channels (10) are led through the support plate (2) from the edge of the measurement zone (4).

23. The device according to claim 1, characterized in that drainage channels (10) are led through the support plate (2) from the edge of the measurement zone (4).

24. A method for measuring a three-dimensional surface structure (9), by producing a silicone impression of the surface structure (9) by means of a transparent support plate (2) for receiving initially liquid silicone material (3) and by analyzing the hardened silicone impression in an optical analyzer for the surface structure (9), characterized by providing a double-sided adhesive sheet (7) in which a measurement zone (4) and at least one drainage channel (10) for excess silicone material (3) are punched out, sticking the adhesive sheet (7) relative to the surface structure (9), applying uniformly colored silicone material (3) onto the surface structure (9) surrounded by the measurement zone (4), placing a transparent pane (5) onto the sheet (7), excess silicone material (3) being capable of escaping from the measurement zone (4) via the drainage channel (10), and the support plate (2) with the pane (5), the sheet (3) and the silicone impression in the measurement zone (4) are removed and analyzed in an optical analyzer after the silicone material (3) is hardened.

25. The method according to claim 24, characterized in that the analysis of the silicone impression is effected through a light intensity measurement of the light absorption of the silicone impression, comparative values being obtained by a calibrating means (6) for each charge of the colored silicone material (3) by producing, in a step-like manner, different defined layer sizes of the colored silicone material (3).

* * * * *